United States Patent [19]

Roeschert et al.

[11] Patent Number: 6,063,545
[45] Date of Patent: May 16, 2000

[54] NEGATIVE-WORKING RADIATION-SENSITIVE MIXTURE, AND RADIATION-SENSITIVE RECORDING MATERIAL PRODUCED WITH THIS MIXTURE

[75] Inventors: Horst Roeschert, Ober-Hilbersheim; Juergen Fuchs, Wicker; Walter Spiess, Dieburg; Charlotte Eckes, Mainz; Georg Pawlowski, Wiesbaden, all of Germany; Ralph Dammel, Coventry, R.I.

[73] Assignee: Clariant GmbH, Frankfurt, Germany

[21] Appl. No.: 07/871,032

[22] Filed: Apr. 20, 1992

[30] Foreign Application Priority Data

Apr. 20, 1991 [DE] Germany .............................. 41 12 974

[51] Int. Cl.$^7$ ...................................................... G03C 1/73
[52] U.S. Cl. ................................... 430/280.1; 430/270.1; 430/325; 430/921
[58] Field of Search .................................. 430/271, 270, 430/280, 270.1, 280.1, 325

[56] References Cited

U.S. PATENT DOCUMENTS

| | | | |
|---|---|---|---|
| 3,692,560 | 9/1972 | Rosenkranz | 528/128 |
| 3,770,438 | 11/1973 | Celeste | 430/53 |
| 4,840,867 | 6/1989 | Elsaesser et al. | 430/156 |
| 4,994,346 | 2/1991 | Meier et al. | 430/280.1 |
| 5,118,582 | 6/1992 | Ueno et al. | 430/270.1 |

FOREIGN PATENT DOCUMENTS

| | | | |
|---|---|---|---|
| 164248 | 12/1985 | European Pat. Off. . | |
| 232972 | 8/1987 | European Pat. Off. . | |
| 0 302 019 | 2/1989 | European Pat. Off. . | |
| 0388813 | 3/1990 | European Pat. Off. | 430/270.1 |
| 0 388 343 | 9/1990 | European Pat. Off. . | |
| 0 388 813 | 9/1990 | European Pat. Off. . | |
| 0 407 086 | 1/1991 | European Pat. Off. . | |
| 0419147 | 3/1991 | European Pat. Off. . | |
| 0 444 493 | 9/1991 | European Pat. Off. . | |
| 3930087 | 3/1991 | Germany . | |
| 60-45241 | 4/1985 | Japan | 430/270.1 |
| 60-045241 | 11/1985 | Japan | 430/270.1 |
| 60-230136 | 11/1985 | Japan | 430/270.1 |
| 1-293339 | 11/1989 | Japan . | |
| 0419147 | 3/1991 | Japan | 430/270.1 |

OTHER PUBLICATIONS

F.M. Houlihan, "An Evaluation of Nitrobenzyl Ester Chemistry for Chemical Amplification Resists", SPIE Proc., Adv. in Resist Techn. and Proc., vol. 920, 1988, pp. 67–74.

C.G. Willson, "Organic Resist Materials—Theory and Chemistry", Introduction to Microlithography ACS Symp. Ser. 219, 1983, pp. 88–159.

J. Crivello, "Possibilities for Photoimaging Using Onium Salts", Polym. Eng. Sci., vol. 23, No. 17, 1983, pp. 953–956.

T. Ueno et al., "Chemical Amplification Positive Resist Systems Using Novel Sulfonates as Acid Generators", Polymers for Microelectronics—Science and Technology, 1989, pp. 66–67.

Peter, et al., "A New Photoinitiator System For Radical and Cationic Polymerization", Chemical Abstracts, vol. 92, Jun. 16, 1980, p. 6, Abstract No. 198859C.

F.M. Houlihan et al, "An Evaluation of Nitrobenzyl Ester Chemistry for Chemical Amplification Resists," SPIE Proc., Adv. in Resist Techn. and Proc., vol. 920, 1988, pp. 67–74.

T. Ueno et al, "Chemical Amplification Positive Resist System Using Novel Sulfonatesos Acid Generators," Polymers for Microelectronics—Science and Technology, 1989, pp. 66–67.

Primary Examiner—Bernard Codd
Attorney, Agent, or Firm—Foley & Lardner

[57] ABSTRACT

A negative-working radiation-sensitive mixture containing
a) a compound which generates a strong acid under the action of actinic radiation,
b) a compound having at least two groups crosslinkable by means of acid and
c) a polymeric binder which is insoluble in water and soluble or at least swellable in aqueous alkaline solutions,
wherein the compound (a) comprises a di-, tri- or tetra-hydroxybenzene which may be further substituted, or a polymer containing a di-, tri-, or tetra- hydroxy phenyl radical, is esterified with respectively 2, 3 or 4 sulfonic acids of the formula R—SO$_3$H, and is distinguished by high resolution and high sensitivity over a wide spectral range. It also shows high thermal stability and does not form any corrosive photolysis products on exposure. A radiation-sensitive recording material produced with this mixture is suitable for the production of photoresists, electronic components, printing plates or for chemical milling.

21 Claims, No Drawings

NEGATIVE-WORKING RADIATION-SENSITIVE MIXTURE, AND RADIATION-SENSITIVE RECORDING MATERIAL PRODUCED WITH THIS MIXTURE

BACKGROUND OF THE INVENTION

1. Field of the Invention

The invention relates to a negative-working radiation sensitive mixture comprising a) a compound which generates a strong acid under the action of actinic radiation,
b) a compound having at least two groups crosslinkable by means of acid, and
c) a polymeric binder which is insoluble in water and soluble or at least swellable in aqueous alkaline solutions.

The invention also relates to a radiation-sensitive recording material produced with this mixture which is suitable for producing photoresists, electronic components, printing plates, or for chemical milling. 2. Description of Related Art The continuing reduction in the size of the structures, for example, in chip manufacture down into the range of less than 1 μm, requires modified lithographic techniques to form such structures. To form images of such fine structures, radiation of a short wavelength is used, such as high-energy UV light, electron beams, and X-rays. The radiation-sensitive mixture must be adapted to the short-wave radiation. A compilation of the requirements to be met by the radiation-sensitive mixture is given in the article by C. G. Willson "Organic Resist Materials—Theory and Chemistry" [Introduction to Microlithography, Theory, Materials, and Processing, editors L. F. Thompson, C. G. Willson, M. J. Bowden, ACS Symp. Ser., 219, 87 (1983), American Chemical Society, Washington].

There is therefore an increased demand for radiation-sensitive mixtures which can be used in the more recent technologies, such as mid-UV or deep-UV lithography having an exposure, for example, with excimer lasers at wavelengths of 305 nm (XeF), 248 nm (KrF), 193 nm (ArF), electron beam lithography or X-ray lithography, and which, furthermore, are preferably sensitive in a wide spectral region and correspondingly can also be used in conventional UV lithography.

Negative-working radiation-sensitive mixtures which contain bisazides as crosslinking agents and binders derived from isoprene are known. They are used as radiation-sensitive layers in the production of printing plates, printed circuits, and integrated circuits. Their use in microlithography is, however, restricted by various technical disadvantages. Thus, it is difficult to produce qualitatively high-grade layers without pinholes. Also, the heat holdout of such mixtures is inadequate, i.e., the resist images are distorted by thermal flow during processing. Finally, their resolution capacity is restricted to structures of >2 μm since, during the necessary development with organic solvents, they show undesirably high swelling even in the hardened areas, which in turn causes structure distortions or inhomogeneous developing processes and hence inadequate reproduction of the image predetermined by the exposure mask.

To be able to produce resist images having a resolution of better than 2 μm, other negative-working radiation-sensitive mixtures have been developed which are sensitive to radiation of shorter wavelength, for example to high-energy UV radiation, electron beams, or X-rays. Such a mixture contains, for example, a copolymer of 2,3-epoxypropyl methacrylate and 2,3-dichloropropyl methacrylate (DCOPA) or a combination of the corresponding homopolymers. The glass transition temperature of this mixture is, however, too low for many applications and, in particular, the low resistance of the mixture to plasma etching is undesirable. Furthermore, even this resist material must be processed using developers based on organic solvents which are prone to pollute the environment. Other known negative-working, aliphatically based photoresists also show a low resistance to plasma etching.

In EP-A 0,164,248, an acid-curable mixture was described which can be developed in aqueous alkaline media, has an improved plasma-etching resistance due to the use of aromatics and is sensitive to near UV light, that is, 350 to 450 nm. The acid generators mentioned here are especially sulfonic acid ester derivatives of diazonaphthoquinone, which form weakly acidic carboxylic acids on exposure and are therefore effective only in a comparatively high concentration. Due to the weak absorptions and the inadequate bleaching properties of the photolytic acid generator, however, such mixtures have a low sensitivity to DUV radiation, electron beams and X-rays.

In U.S. Pat. No. 3,692,560, an acid-curable mixture is described which contains an acid-crosslinkable melamine derivative, a novolak and chlorinated benzophenones as photolytic acid generators. These mixtures again do not have an adequate sensitivity in the deep UV region. Furthermore, hydrohalic acids are undesired as crosslinking catalysts, since these can, during the subsequent doping processes, undergo reactions with the dopants. Moreover, hydrohalic acids remaining in the cured resist have a strong corrosive action and can cause destruction of the material to be imaged and of the production equipment.

The same applies to the acid-generating derivatives of DDT, mentioned in EP 0,232,972, which are highly toxic and, if only for this reason, are not suitable for practice. Nevertheless, such compounds show a considerable sensitivity in the deep UV region (200 to 300 nm).

As the compounds which generate a strong acid on irradiation, especially onium salts, such as diazonium, phosphonium, sulfonium and iodonium salts of non-nucleophilic acids such as $HSbF_6$, $HAsF_6$ or $HPF_6$, as described in J. V. Crivello, Polym. Eng. Sci., 23 (1983) 953 have hitherto been used. In addition, halogen compounds, especially trichloromethyltriazine derivatives or trichloromethyloxadiazole derivatives, o-quinonediazidesulfonyl chlorides, o-quinonediazide-4sulfonic acid esters, organometal/organoihalogen combinations, bis(sulfonyl)diazomethanes, sulfonylcarbonyldiazomethanes (See DE-A 3,930,087) or nitrobenzyl tosylates described by F. M. Houlihan et al., SPIE Proc., Adv. in Resist Techn. and Proc. 920 (1988) 67 have been recommended.

These compounds are used in negative- or positive-working radiation-sensitive mixtures. The use of such photolytic acid generators involves, however, certain disadvantages which drastically restrict the possible uses thereof in various fields of application. For example, many of the onium salts are toxic and their solubility is inadequate in many solvents. Hence only a few solvents are suitable for preparing a coating solution. Furthermore, when the onium salts are used, undesired foreign atoms are sometimes introduced which can cause interference with the process, especially in microlithography. Moreover, the onium salts form Brönstedt acids, which have a very severe corrosive action in the photolysis. These acids attack sensitive substrates, so that the use of such mixtures leads to unsatisfactory results. The halogen compounds and also the quinonediazidesulfonic acid chlorides also form hydrohalic acids which have a severely corrosive action. In addition, such compounds also have only a limited storage life on certain substrates.

This storage life was improved by inserting an interlayer between the substrate and the radiation-sensitive layer containing compounds of the type (a), but this led to an undesired increase in defects and to diminished reproducibility (See DE-A 3,621,376, equivalent to U.S. Pat. No. 4,840,867).

In more recent papers by F. M. Houlihan et al., SPIE 920, 67 (1988), it was shown by reference to positive-working systems that, in addition to the above-mentioned acid generators, nitrobenzyl tosylates, which on exposure also generate sulfonic acids having a low migration tendency, can be used in certain acid-unstable resist formulations. It can be deduced from these results that such compounds can also be used for photo-curable systems. However, the sensitivities thus achieved and the thermal stability of the photoresists proved to be inadequate.

It is also known from T. Ueno et al., Chemical Amplification Positive Resist Systems Using Novel Sulfonates as Acid Generators, in "Polymers for Microelectronics—Science and Technology", edited by Y. Tabata et al., Kodansha-Weinheim-New York, 1989, pages 66–67, to use 1,2,3-trihydroxybenzene fully esterified with methane-, ethane-, propane-, butane-, benzene-, toluene- or naphthalene-sulfonic acid as a photo-active acid generator in positive-working photoresist systems. However, these resist systems are not used in practice, since their thermal stability and plasma-etching resistance are inadequate and, after development, resist remnants in the grooves and unacceptable resist profiles are observed.

In spite of the intensive research activity so far carried out in this field, no radiation-sensitive mixture is at present known, by means of which a negative-working radiation-sensitive recording material can be produced which has a high sensitivity in the DUV region, that is, 200 to 300 nm, and high resolution, and which, on irradiation, does not release an acid which has a corrosive action, and can be developed in aqueous alkaline media.

SUMMARY OF THE INVENTION

It was therefore an object of the invention to provide a radiation-sensitive mixture based on acid-generating compounds in combination with acid-crosslinkable compounds, wherein the compound photolytically generating an acid should be as stable as possible on all known substrates and, as the photoproduct, gives an acid not having a corrosive action.

It is also an object of the present invention to provide a negative-working recording material which contains such a radiation-sensitive mixture, and gives a defect-free, negative image of the mask, and to provide a process for producing such a recording material.

It is also an objective of the invention to provide a method of preparing an image pattern using the recording material.

There is further provided a negative-working radiation-sensitive mixture comprising:

a) at least one compound which generates a strong acid under the action of actinic radiation, selected from a di-, tri- or tetrahydroxybenzene optionally substituted by one or more radicals R', or a polymer containing at least one di-, tri-, or tetra-hydroxy phenyl radical which is partially or fully esterified with sulfonic acids of the formula R-SO$_3$H, where R and R' may be the same or different and R is a ($C_1$–$C_{10}$)alkyl, ($C_5$–$C_{10}$)cycloalkyl, ($C_6$–$C_{10}$)aryl, ($C_6$–$C_{10}$)aryl($C_1$–$C_{10}$)alkyl or ($C_3$–$C_9$) heteroaryl radical, any of which may be further substituted, and R' is one of the radicals given for R or is a ($C_1$–$C_{10}$)alkanoyl, ($C_1$–$C_{16}$)alkoxycarbonyl or (C7–$C_{11}$)aroyl radical, any of which may be substituted, b) at least one compound having at least two groups crosslinkable by means of said strong acid, and c) at least one polymeric binder which is insoluble in water and soluble or at least swellable in an aqueous alkaline solution.

There has also been provided a negative-working radiation-sensitive recording material comprising a substrate and a radiation-sensitive layer which comprises such a mixture.

There has also been provided a process for producing the recording material comprising applying the mixture to said substrate so as to form a radiation-sensitive layer.

There has also been provided a method of preparing an image pattern comprising irradiating the radiation-sensitive layer imagewise, optionally heating the irradiated layer, treating the layer with a developer so as to wash away the unexposed areas, and optionally post-hardening the developed structure.

Further objects, features, and advantages of the present invention will become apparent from the detailed description of preferred embodiments that follows.

DETAILED DESCRIPTION OF THE PREFERRED EMBODIMENTS

Any sulfonic acid R—SO$_3$H known in the art can be used to esterify the hydroxybenzene. Examples of suitable sulfonic acids R—SO$_3$H are methanesulfonic acid, ethanesulfonic acid, propanesulfonic acid, isopropanesulfonic acid, butanesulfonic acid, sec.-butanesulfonic acid, isobutanesulfonic acid, tert.-butanesulfonic acid, pentanesulfonic acid, hexanesulfonic acid, octanesulfonic acid, cyclohexanesulfonic acid, phenylmethanesulfonic acid, 2-phenylethanesulfonic acid, 3-phenylpropanesulfonic acid, benzenesulfonic acid and naphthalenesulfonic acid.

Heteroaromatic sulfonic acids are also suitable. The heteroarylsulfonic acids preferably have 4 to 9 carbon atoms, and an aromatic oxygen atom or sulfur atom or 1 or 2 aromatic nitrogen atoms. Examples of these are furansulfonic, thiophenesulfonic, pyrrolesulfonic, pyridinesulfonic, pyrimidinesulfonic, and pyrazinesulfonic acids. Sulfonic acids having a binuclear heteroaryl radical are also suitable. Examples, include benzofuransulfonic, isobenzofuransulfonic, benzo [b]thiophenesulfonic and indolesulfonic acids. However, the nitrogen-containing heterocyclic compounds must not be basic for use in the present invention, since, otherwise, the acid generated in the photoreaction is neutralized by the heterocyclic radical and, as a consequence of this, the efficiency of the acid-catalyzed reaction would be drastically reduced. Basicity is, for example, counterbalanced by appropriate substituents at the nitrogen atoms.

The radicals R and R' may individually be substituted or unsubstituted. In principle, the substituents can be any which do not undergo undesired reactions. Suitable substituents are linear and branched alkyl groups having preferably not more than 8 carbon atoms, especially not more than 6 carbon atoms, such as methyl, ethyl, propyl, isopropyl, butyl, sec.-butyl, isobutyl and tert.-butyl. The alkyl groups can be fluorinated and preferably also perfluorinated. Of the perfluorinated alkyl radicals, trifluoromethyl and perfluorobutyl are particularly suitable. Further suitable substituents include ($C_1$–$C_8$)alkoxy, ($C_1$–$C_8$)alkoxy-($C_1$–$C_8$)alkoxy, ($C_1$–$C_8$)alkanoyl, ($C_1$–$C_8$)alkanoyloxy, ($C_1$–$C_8$)

alkanoylamino, $(C_6-C_{10})$aryl, $(C_6-C_{10})$aryloxy, $(C_6-C_{10})$aryl-$(C_1-C_8)$alkoxy, $(C_6-C_{11})$aroylamino, $(C_6-C_{11})$aroylamino-$(C_1-C_6)$alkyl, cyano and halogen. More than one of these substituents may be present. Independently thereof, different substituents can be present side by side. Preferred substituents are $(C_1-C_4)$alkyl, $(C_1-C_4)$alkoxy and phenyl. The phenyl radical is in turn preferably substituted by $(C_1-C_6)$alkyl, $(C_1-C_8)$perfluoroalkyl and/or halogen, in particular fluorine. Preferably, one of these substituents is in the paraposition.

The preferred substituent for R' include methyl, ethyl, propyl, isopropyl, butyl, sec.-butyl, isobutyl, tert.-butyl, formyl, acetyl, methoxycarbonyl, phenyl, benzyl, cyclohexyl, benzoyl, phenethyl, 3-phenylpropyl, [1]naphthyl or [2]naphthyl. Heteroaryl radicals may also be used as substituents. The heteroaryl radicals have, in addition to 4 to 9 carbon atoms, also an aromatic oxygen or sulfur atom or 1 or 2 nitrogen atoms. Examples are furanyl, thiophenyl, pyrrolyl, pyridinyl and quinolinyl radicals, with the proviso that, for the reasons indicated above, the nitrogen containing heterocyclic compounds must not be basic.

The radicals R' can be substituted in the same way as the radicals R. Furthermore, they can also be substituted by hydroxy and sulfonyloxy that is, O—SO$_2$—R, R being as defined above. The aromatic radicals R' are preferably substituted by $(C_1-C_4)$alkoxy, $(C_1-C_8)$alkanoyl, sulfonyloxy and/or halogen. If several substituents are bound to one aromatic radical, these are preferably selected from $(C_1-C_4)$ alkyl, hydroxyl, sulfonyloxy and/or halogen.

In addition to di-, tri- and tetra-hydroxybenzenes, polymers containing di-, tri- and tetra-hydroxyphenyl radicals are also suitable as a starting material for preparing the multifunctional sulfonic acid esters. Such polymers contain, for example, units derived from dihydroxyphenyl (meth) acrylate. Units without a dihydroxyphenyl radical can be present side by side with units with this radical, i.e., in addition to homopolymers, copolymers and terpolymers as well as polymers with even more different units are suitable. The further units are preferably derived from styrene, hydroxystyrene, maleimide, N-substituted maleimide, a vinyl alkyl ether and/or a vinyl-alkyl-silane. Homopolymers and copolymers, especially copolymers with maleimide or styrene, are preferred. Condensation products of a trihydroxybenzene, such as 1,2,3- and 1,2,4-trihydroxybenzene, with a ketone are likewise suitable as starting materials. Aldehydes may also be used as partners in the condensation reaction, but they are not preferred. The condensation products have a structure similar to that of novolak resins. Multifunctional sulfonic acid esters from polymeric starting materials are, however, generally not preferred.

Preferred sulfonic acids are methanesulfonic, trichloromethanesulfonic, trifluoromethanesulfonic, ethanesulfonic, trifluoroethanesulfonic, propanesulfonic, isopropanesulfonic, 3-chloropropanesulfonic, butanesulfonic, isobutanesulfonic, perfluorobutanesulfonic, hexanesulfonic, perfluorohexanesulfonic, cyclohexanesulfonic, octanesulfonic, perfluorooctanesulfonic, phenylmethanesulfonic, 2-phenylethanesulfonic, 3-phenylpropanesulfonic, benzenesulfonic, 3-perfluorooctylbenzenesulfonic, 4-trifluoromethylbenzenesulfonic, 4-perfluorobutylbenzenesulfonic, 4-tolylsulfonic, 4bromobenzenesulfonic, 4-cyanobenzenesulfonic, 4-tert.-butylbenzenesulfonic, 2,4,5-trimethylbenzenesulfonic, 3,4-dichlorobenzenesulfonic, (+)camphor-10-sulfonic and 2-benzoylaminomethyl-thiophene-5-sulfonic acids.

Particularly suitable starting compounds with phenolic hydroxy groups which are esterified with the sulfonic acid include: pyrocatechol, resorcinol, hydroquinone, 2,4-dihydroxybenzaldehyde, 3,4-dihydroxybenzaldehyde, 3,5-dihydroxybenzaldehyde, poly[2,3dihydroxyphenyl methacrylate], poly[3,5-dihydroxyphenyl methacrylate], poly[2,4-dihydroxyphenylmethacrylate], 2,4,2',4'-tetrahydroxybenzophenone, 2,4,4'-trihydroxybenzophenone, 2,4-dihydroxybenzophenone, pyrogallol, phloroglucinol, 1,2,4-trihydroxybenzene, 2,3,4-trihydroxybenzaldehyde, gallusaldehyde, methyl gallate, propyl gallate, octyl gallate, dodecyl gallate, 2,3,4-trihydroxybenzophenone, 2,4,6-trihydroxybenzophenone, 2,3,4-trihydroxyacetophenone, 2,4,6-trihydroxyacetophenone, 1-octanoyl-2,3,4-trihydroxybenzene, 1-hexanoyl-2,3,4-trihydroxybenzene, 1-butyryl-2,3,4trihydroxybenzene, 1-octanoyl-2,4,6-trihydroxybenzene, 1hexanoyl-2,4,6-trihydroxybenzene, 1-butyryl-2,4,6trihydroxybenzene and also condensation products of pyrogallol and ketones. Di- and tri-hydroxybenzenes or polymers containing di- and tri-hydroxyphenyl groups are generally preferred. The products may be incompletely or fully esterfied, although fully esterfied products are generally preferred. However, incompletely esterified products, i.e., those which still contain free phenolic hydroxy groups, are more soluble in special radiation-sensitive mixtures and are sometime preferred.

The suitability of the sulfonic acid esters according to the invention in negative-working mixtures was unexpected since, upon irradiation, they give soluble cleavage products, i.e., phenols and sulfonic acids in the areas to be crosslinked.

The preparation of the multifunctional sulfonic acid esters used in the mixture according to the invention is known per se. Any process known in the art may be used to prepare the ester. The starting materials used here are above all the corresponding sulfonic acid chlorides. Numerous examples of processes for preparing aromatic sulfonic acid esters are described, for example, by F. Muth in: Houben-Weyl-Müller, Methoden der organischen Chemie [Methods in Organic Chemistry], vol IX, page 633 (and references cited therein), Thieme-Verlag, 4th edition, Stuttgart 1955, and by S. Pawlenko, loc. cit., volume E11, page 1084, Thieme-Verlag, 1st edition, Stuttgart 1985, and in the patent literature. The corresponding sulfonic acid anhydrides are also suitable starting materials (see S. Pawlenko, loc. cit., volume E11, page 1086, Thieme-Verlag, 1st edition, Stuttgart 1985, and P. J. Stang, M. Hanack and L. R. Subramaniam, Synthesis, 1982,85). This applies in particular to the benzenesulfonic acid anhydrides substituted by perfluoroalkyl groups.

The multifunctional sulfonic acid esters in which R is a trifluoromethyl, trifluoroethyl, a higher trifluoroalkyl or a perfluoroalkyl radical or a perfluoroalkyl-substituted phenyl radical were, in contrast to the other sulfonic acid esters described, prepared by reacting the corresponding sulfonic acid fluorides with the trimethylsilanyloxybenzenes by the process indicated by H. Niederprüm, V. Beyl and P. Voss (Liebigs Ann. Chem. 1973, 20). The trimethylsilanyloxy derivatives of the di-, tri- and tetra-hydroxybenzenes are obtained by reaction with hexamethyldisilazane analogously to the processes described in the monographs by E. W. Colvin, Silicon Reagents in Organic Synthesis, 1st edition, pages 91–97, Academic Press, London 1988, and T. W. Greene, Protective Groups in Organic Synthesis, 1st edition, page 100, J. Wiley & Sons, New York 1981.

The radiation-sensitive mixture according to the invention is distinguished by a high sensitivity over a wide spectral range. It shows high thermal stability and makes it possible to reproduce extremely fine structures of an original in true detail. The acid generated on irradiation does not have a corrosive action, so that the mixture can also be used on sensitive substrate materials. surprisingly, the negative-working, radiation-sensitive mixtures according to the invention show not only a high thermal stability and plasma-etching resistance but also outstanding lithographic properties which permit resolution in the half-micrometer range and in some cases also in the sub-half-micrometer range. After imagewise irradiation and subsequent development, a negative image of the mask in true detail is obtained. The resist fields have steep flanks. In the unirradiated areas, the resist layer is completely detached, i.e., no remnants or residues of the layer remain on the substrate. The sulfonic acids generated in the photolysis lead to efficient crosslinking of the resist components b) and c), which permits the production of highly sensitive, negative-working mixtures.

Recording materials produced with the mixtures according to the invention show, surprisingly, an image differentiation which satisfies the most stringent requirements and, even more surprisingly, an improvement in contrast and resolving power. For example, the mixtures according to the invention allow the production of a highly sensitive negative-working photoresist for high-energy UV2 radiation, for example, 248 nm.

Since the mixture according to the invention is sensitive over a wide spectral range, generally any actinic radiation is suitable for imagewise irradiation. In this context, actinic radiation is to be understood as any radiation whose energy corresponds at least to that of short-wave visible light. In this case, UV radiation in the range from 190 to 450 nm, preferably from 200 to 400 nm, particularly preferably from 200 to 300 nm, and also electron beams or X-rays are particularly suitable.

The multifunctional sulfonic acid esters contained in the radiation-sensitive mixture according to the invention and generating an acid on irradiation can be used alone or in combination with other acid generators. Any known acid generators, or combination of acid generators can be used. Suitable additional acid generators are especially the multifunctional sulfonic acid esters of 2,4,6-tris-(2-hydroxyethoxy)-[1,3,5]-triazine, described in Attorneys Docket Number 16878/443 which is equivalent to German Patent Application P 41 12 972.5 filed concomitantly, which is hereby incorporated by reference.

Furthermore, the multifunctional sulfonic acid esters can be combined with onium salts, halogen compounds, especially trichloromethyltriazine derivatives or trichloromethyloxadiazole derivatives, 1, 2-disulfones, o-quinonediazidesulfonyl chlorides or organometal/organohalogen combinations. Mixtures with bis(sulfonyl)-diazomethanes and sulfonyl-carbonyldiazomethanes are also possible. In such mixtures, however, the above-mentioned disadvantages associated with the additional acid generators may reappear.

Any amount of multifunctional sulfonic acid esters in the mixture according to the invention can be used depending on the intended use of the mixture. In general 0.5 to 25% by weight, preferably 3 to 15% by weight, relative to the total weight of the solids in the mixture is used.

Any compound known in the art can be used as b), so long as it contains at least two groups crosslinkable by the acid released by a). The acid-crosslinkable compounds b) used are especially the resols disclosed in GB 2,082,339. Also aromatics substituted by alkoxymethyl or oxiranylmethyl groups disclosed in EP-A 0,212,482 and monomeric and oligomeric melamine/formaldehyde condensates and urea/formaldehyde condensates disclosed in EP-A 0,133,216, DE-A 3,634,671, and DE 3,711,264 are preferred. Examples of the first type are the commercially available resol products Bakelite R 5363, Bakelite R 17620, Bakelite R 10282 and Kelrez 40-152. Bakelite and Kelrez are registered trademarks. However, resol derivatives are not altogether preferred, since they show relatively high absorptions in the deep UV region and thus cause an impairment of the image reproduction.

More suitable crosslinkable compounds are those known from EP-A 0,212,482, which is hereby incorporated by reference, having the formula I

$$(R^1O\text{---}CHR^3)_n\text{---}A\text{---}(CHR^3\text{---}OR^2)_m \qquad (I)$$

in which

A is —B— or —B—Y—B— and

B is a substituted or unsubstituted mononuclear carbocyclic or oxygen- or sulfur-containing heterocyclic aromatic compound, Y is a single bond, $(C_1\text{-}C_4)$alkylene or $(C_1\text{-}C_4)$ alkylenedioxy, whose chains can be interrupted by —O—, —S—, —SO$_2$—, —CO—, —CO$_2$—, —O—CO$_2$—, —CONH— or O—C$_6$H$_4$—O —, $R^1$ and $R^2$ are the same or different and are hydrogen, $(C_1\text{-}C_6)$alkyl, $C_5$- or $C_6$-cycloalkyl, substituted or unsubstituted $(C_6\text{-}C_{12})$aryl, $(C_6\text{-}C_{12})$aralkyl or acyl, $R^3$ is hydrogen, $(C_1\text{-}C_4)$alkyl or substituted or unsubstituted phenyl, n is an integer from 1 to 3 and m is an integer from 0 to 3, wherein n+m is at least 2.

Typical crosslinkable compounds b) are accordingly carbocylic and heterocyclic aromatics compounds which are polysubstituted by hydroxymethyl, acetoxymethyl and/or methoxymethyl groups.

Further preferred crosslinkable compounds are melamine/formaldehyde derivatives which have, for example, at least two free N-hydroxymethyl, N-alkoxymethyl or N-acyloxymethyl groups. In particular the N-alkoxymethyl derivatives are suitable for use in the radiation-sensitive mixture according to the invention.

The crosslinkable compounds are capable of crosslinking with the polymeric binders at elevated temperatures under the action of the photolytically generated acid. The general feature is that they can form a carbonium ion under the said conditions of temperature and acid.

Any amount of b) can be used so long as the desired crosslinking is obtained. The content of the acid-crosslinkable compound b) is expediently 1 to 50% by weight, preferably 5 to 25% by weight, each relative to the total weight of the solid constituents of the mixture.

The radiation-sensitive mixture according to the invention also contains at least one polymeric binder c) which is insoluble in water, but soluble or at least swellable in aqueous alkaline solutions. Any binder or combination of binders having these characteristics is useful. The binder is in particular distinguished by good compatibility with the other constituents of the radiation-sensitive mixture according to the invention and especially by the lowest possible characteristic absorption, i.e., a high transparency, in the wavelength range from 190 to 300 nm. Binders based solely on novolak condensation resins, which are generally used in combination with naphthoquinonediazides as photoactive components, do not meet this condition. Although novolak condensation resins show in the unexposed areas a decrease in the solubility in aqueous alkaline developers after imagewise exposure, their characteristic absorption in the range of the short wavelength desired for the irradiation is undesirably high.

However, novolak condensation resins can be used in a mixture with other resins of higher transparency. The mixing ratios here depend predominantly on the nature of the binder to be mixed with the novolak resin. Especially important factors are the degree of characteristic absorption of the binder in the said wavelength range, and also the miscibility with the other constituents of the radiation-sensitive mixture. In general, however, the binder of the radiation-sensitive mixture according to the invention preferably contains at most 30% by weight, especially at most 20% by weight, of a novolak condensation resin.

The binder c) advantageously has an extinction of less than <0.5 $\mu m^{-1}$, preferably <0.3 $\mu m^{-1}$, for radiation of 248 nm wavelength.

Suitable binders are homopolymers or copolymers of p-hydroxystyrene and alkyl derivatives thereof, for example of 3-methyl-4-hydroxystyrene, and homopolymers or copolymers of other vinylphenols, for example of 3hydroxystyrene or esters or amides of acrylic acid with aromatics containing phenolic groups. Polymerizable compounds such as styrene, methyl (meth)acrylate or the like can be used as comonomers.

Mixtures having an increased plasma resistance are obtained when silicon-containing vinyl monomers, for example vinyltrimethylsilane, are also used for the preparation of the binders. The transparency of these binders in the region of interest is in general higher, so that improved structuring is possible.

Equally well, homopolymers or copolymers of maleimide can also be used. These binders too show a high transparency in the wavelength range described. Here again, the comonomers preferably used are styrene, substituted styrenes, vinyl ethers, vinyl esters, vinylsilyl compounds or (meth)acrylates.

Finally, copolymers of styrene can be used with comonomers which effect an increase in solubility in aqueous alkaline solutions. These include, for example, maleic anhydride and maleic acid half-esters.

More than one of the said binders can be mixed if this does not impair the optical quality of the radiation-sensitive mixture. However, binder mixtures are generally not preferred.

The binder content can be varied depending on the intended use of the mixture and is in general 40 to 95% by weight, especially 50 to 90% by weight, relative to the total weight of the solid constituents of the radiationsensitive mixture.

If appropriate, at least one of dyes, pigments, plasticizers, wetting agents, flow agents, and also polyglycols and cellulose ethers, for example ethylcellulose, can also be added to the radiationsensitive mixtures according to the invention in order to meet special requirements, such as flexibility, adhesion and gloss.

Any known substrate can be coated with the mixture according to the invention. When a substrate is to be coated with the radiation-sensitive mixture according to the invention any known coating process can be used. The mixture is expediently dissolved in a solvent or in a combination of solvents prior to coating. Ethylene glycol and propylene glycol and the monoalkyl and dialkyl ethers derived from them, especially the monomethyl and dimethyl ethers and the monoethyl and diethyl ethers, esters derived from aliphatic ($C_1$–$C_6$)carboxylic acids and either ($C_1$–$C_8$)alkanols or ($C_1$–$C_8$)alkanediols or ($C_1$–$C_6$)alkoxy-($C_1$–$C_8$)alkanols, for example ethyl acetate, hydroxyethyl acetate, alkoxyethyl acetate, n-butyl acetate, propylene glycol monoalkyl ether-acetate, especially propylene glycol methyl ether-acetate and amyl acetate, ethers such as tetrahydrofuran and dioxane, ketones such as methyl ethyl ketone, methyl isobutyl ketone, cyclopentanone and cyclohexanone, N,N-dialkyl-carboxylic acid amides such as N,N-dimethylformamide and N,N-dimethylacetamide, and also hexamethyl-phosphotriamide, N-methyl-pyrrolidin-2-one and butyrolactone, and also any desired mixtures of these, are particularly suitable for this purpose. Amongst these, the glycol ethers, aliphatic esters and ketones are particularly preferred.

Ultimately, the choice of the solvent or solvent mixture depends on the coating process used, on the desired layer thickness and on the drying conditions. The solvents must also be chemically inert to the other layer constituents under the conditions used.

The solution prepared with the said solvents generally has a solids content from 5 to 60% by weight, preferably up to 50% by weight.

The invention also relates to a radiation-sensitive recording material comprising a substrate and, located thereon, a radiation-sensitive layer containing the mixture according to the invention.

Possible substrates are all those materials of which capacitors, semiconductors, multi-layer printed circuits or integrated circuits are composed, or from which these can be produced. Silicon substrates which can also be thermally oxidized and/or coated with aluminum, and also doped, merit special mention. In addition, all other substrates usual in semiconductor technology are possible, such as silicon nitride, gallium arsenide and indium phosphide. Moreover, the substrates known from liquid crystal display manufacture are possible, such as, for example, glass or indium-tin oxide, and also metal plates and foils—for example of aluminum, copper, zinc foils, bimetal and trimetal foils, and also electrically non-conductive foils on which metals have been vapor-deposited, and paper. These substrates can be thermally pretreated, superficially roughened, incipiently etched or, to improve desired properties, for example to enhance the hydrophilic character, pretreated with chemicals.

To impart better cohesion and/or better adhesion of the radiation-sensitive layer to the substrate surface, the layer can contain an adhesion promoter. In the case of silicon or silica substrates, adhesion promoters of the aminosilane type such as, for example, 3-aminopropyltriethoxysilane or hexamethyldisilazane, can be used for this purpose. Also, a layer containing an adhesive promoter can be applied to the substrate, prior to applying the radiation-sensitive layer.

Suitable supports for the production of photomechanical recording layers, such as printing forms for letterpress printing, planographic printing, screen printing and flexographic printing, are in particular aluminum plates, which may have been anodically oxidized, grained and/or silicated beforehand, and also zinc and steel plates which may be chromium-plated, and also plastic films and paper.

The recording material according to the invention is exposed imagewise to actinic radiation. Suitable radiation sources are especially metal halide lamps, carbon arc lamps, xenon lamps and mercury vapor lamps. Likewise, exposure can be carried out with high-energy radiation such as laser radiation, electron beams or X-rays. However, lamps which can emit light of a wavelength from 190 to 260 nm, i.e., especially xenon lamps and mercury vapor lamps, are particularly preferred. Furthermore, laser light sources can also be used, for example excimer lasers, especially KrF or ArF lasers, which emit at 248 and 193 nm respectively. The radiation sources must show adequate emission in the said wavelength ranges.

The thickness of the light-sensitive layer depends on the intended use. In general, it is between 0.1 and 100 μm, preferably between 0.5 and 10 μm, particularly preferably about 1.0 μm.

The invention also relates to a process for producing a radiation-sensitive recording material. The radiation-sensitive mixture can be applied to the substrate by any known process, including spraying, flow-coating, rolling, whirler-coating and dip-coating. The solvent is then removed by evaporation, so that the radiation-sensitive layer remains on the surface of the substrate. The removal of the solvent can be promoted by heating the layer to temperatures of up to 150° C. The mixture can, however, also be first applied in the above-mentioned way to a temporary support, from which it is transferred under pressure and at an elevated temperature to the final support material. The materials used as temporary support can in principle be all those which are also suitable as support materials. Subsequently, the layer is irradiated imagewise. The layer is then treated with a developer solution which dissolves and removes the unexposed (non-irradiated) areas of the layer, so that a negative image of the original used in the imagewise irradiation remains on the substrate surface.

Any known developer can be used. Suitable developers are especially aqueous solutions which contain silicates, metasilicates, hydroxides, hydrogen phosphates and dihydrogen phosphates, carbonates or hydrogen carbonates of alkali metal ions, alkaline earth metal ions and/or ammonium ions, and also ammonia and the like. Metal ion-free developers are described in U.S. Pat. No. 4,729,941, EP-A 0,062,733, U.S. Pat. No. 4,628,023, U.S. Pat. No. 4,141,733, EP-A 0,097,282 and EP-A 0,023,758. The content of these substances in the developer solution is in general 0.1 to 15% by weight, preferably 0.5 to 5% by weight, relative to the weight of the developer solution. Preferably, metal ion-free developers are used. Small quantities of a wetting agent can have been added to the developers, in order to facilitate the detachment of the soluble areas of the layer.

The developed layer structures can be post-hardened. This is effected in any known manner, in general, by heating on a hotplate up to a temperature below the flow temperature and subsequent exposure of the whole area to the UV light from a xenon-mercury vapor lamp (range from 200 to 250 nm). As a result of the post-hardening, the image structures are crosslinked, so that in general they have a flow resistance up to temperatures of more than 2000C. The post-hardening can also be effected without a temperature increase solely by irradiation with high-energy UV light.

The compounds according to the invention may be used in radiation-sensitive mixtures for the production of integrated circuits or of discrete electrical components by lithographic processes, since they show a high light sensitivity, especially in the case of irradiation with light of a wavelength between 190 and 300 nm. Since the mixtures bleach very well on exposure, a very high resolution can be achieved which is not reached with the known mixtures. The recording material produced from the mixture serves as a mask for the subsequent process steps. Examples of such steps are etching of the layer support, the implantation of ions into the layer support or the precipitation of metals or other materials on the layer support.

The examples described below illustrate the invention without restricting it.

SYNTHESIS EXAMPLE 1,3,5-Tris-methanesulfonyloxy-benzene 39.8 g (0.33 mol) of methanesulfonic acid chloride were added dropwise at 0° C. within the course of 30 minutes to a solution of 12.6 g (0.10 mol) of phloroglucinol and 101 g (1.0 mol) of N-methylmorpholine in 200 ml of dry tetrahydrofuran in such a way that the temperature did not rise above 10° C. After the dropwise addition, the ice bath was removed, and the mixture was warmed to room temperature and stirred for 2 hours at this temperature. The mixture was then slowly added dropwise with continuous stirring to 3 1 of ice water, and the resulting precipitate was filtered off with suction and washed until neutral with water. After drying, this gave 32.9 g (91%) of a colorless powder of melting point 145 to 149° C. Recrystallization from an isopropanol/acetone solvent mixture gave colorless, highly light-refracting platelets of melting point 150° C.

The analysis of this compound gave the following values:
Calculated: C 30.00% H 3.36% S 26.69%
Found: C 29.8% H 3.2% S 26.5%

The multifunctional sulfonic acid esters were characterized by $^1$H and $^{13}$C intense-field nuclear magnetic resonance spectra and by elemental analyses and, if appropriate, IR spectra, to prove the absence of hydroxy groups from the product.

Examples 1 to 8 demonstrate the suitability of the mixture according to the invention for recording materials in microlithography, using very diverse types of energy. By means of Comparison Examples 9 and 10, the superiority of the mixtures according to the invention over the state of the art is demonstrated. Examples 11 and 12 document the applicability of the mixture in printed circuits and planographic printing plates.

APPLICATION EXAMPLES

The coating solutions were filtered through filters of 0.2 μm pore diameter and whirler-coated onto a wafer treated with an adhesion promoter (hexamethyldisilazane). The coater speed of rotation was here selected such that layer thicknesses of about 1.07 μm were obtained after drying for 1 minute at 110° C., on the hotplate.

Unless otherwise stated in the individual examples, the recording material was exposed imagewise under an original to the radiation of a KrF excimer laser (248 nm) or xenon/mercury vapor lamp (260 nm, with interference filter) and then subjected to a post-exposure bake on a hotplate at 110° C. for 1 minute.

Unless otherwise stated, the recording material was developed using a 0.27 N aqueous tetramethylammonium hydroxide solution.

In the examples which follow, parts by weight are abbreviated to p.b.w.

Example 1

A light-sensitive recording material was prepared using a coating solution comprised of 7.5 p.b.w. of a homopolymer of 3-methyl-4-hydroxystyrene, having a softening range of 150° C., 2.5 p.b.w. of a cresol/formaldehyde resol (Bakelite® R5363) and 0.8 p.b.w. of 1,2,3-tris-methanesulfonyloxy-benzene (prepared analogously to the synthesis example) in 42 p.b.w. of propylene glycol monomethyl ether-acetate.

Exposure: 19 mJ/cm$^2$ (xenon/mercury vapor lamp)

Development: 90 seconds

Example 2

A light-sensitive recording material was prepared using a coating solution composed of
8.0 p.b.w. of a 3-methyl-4-hydroxystyrene/p-hydroxystyrene copolymer (molar ratio 75:25) having a softening range of >150° C. and a mean molecular weight of 26,000,
2.0 p.b.w. of hexa-N-methoxymethyl-melamine and
0.4 p.b.w. of 1,3,5-tris-methanesulfonyloxy-benzene (prepared according to the Synthesis Example) in
42 p.b.w. of propylene glycol monomethyl ether-acetate.
Exposure: 21 mJ/cm$^2$ (xenon/mercury vapor lamp)
Development: 90 seconds

Example 3

A light-sensitive recording material was prepared using a coating solution composed of
7.5 p.b.w. of a styrene/maleimide copolymer (molar ratio 50:50) having a softening range from 165 to 180° C.,
2.0 p.b.w. of hexa-N-acetoxymethyl-melamine and 0.4 p.b.w. of 1-octanoyl-2,3,4-tris-(toluene-4-sulfonyloxy)-benzene (prepared analogously to the Synthesis Example) in
42 p.b.w. of propylene glycol monomethyl ether-acetate.
Exposure: 36 mJ/cm$^2$ (xenon/mercury vapor lamp) Post-exposure bake: 2 minutes, 120° C., hotplate
Development: 75 seconds (0.02 N aqueous tetramethylammonium hydroxide solution)

Example 4

A light-sensitive recording material was prepared using a coating solution composed of
7.5 p.b.w. of the copolymer mentioned in Example 3,
2.5 p.b.w. of 4,4'-bis-methoxymethyldiphenyl sulfone and
0.8 p.b.w. of 1,2,3-tris-methanesulfonyloxy-benzene (prepared analogously to the Synthesis Example) in
42 p.b.w. of propylene glycol monomethyl ether-acetate.
Post-bake: 1 minute, 100° C., hotplate
Exposure: 36 mJ/cm$^2$ (xenon/mercury vapor lamp)
Development: 60 seconds (0.02 N aqueous tetramethylammonium hydroxide solution)

Example 5

A light-sensitive recording material was prepared using a coating solution composed of
7.5 p.b.w. of the copolymer mentioned in Example 3,
2.5 p.b.w. of 4,4'-bis-methoxymethyl-diphenyl ether and
0.9 p.b.w. of 1,2,3-tris(4-bromobenzenesulfonyloxy)-benzene (prepared analogously to the Synthesis Example) in
42 p.b.w. of propylene glycol monomethyl ether-acetate.
Exposure: 46 mJ/cm$^2$ (xenon/mercury vapor lamp) Post-exposure bake: 2 minutes, 115° C., hotplate
Development: 75 seconds (0.02 N aqueous tetramethylammonium hydroxide solution)

Example 6

A light-sensitive recording material was prepared using a coating solution composed of
7.5 p.b.w. of a styrene/4-hydroxystyrene copolymer (molar ratio 20:80) having a mean molecular weight of about 32,000,
2.5 p.b.w. of hexa-N-butoxymethyl-melamine and 0.6 p.b.w. of 1,2,4-tris-(1-trifluoromethylethane-sulfonyloxy)-benzene (prepared analogously to the Synthesis Example) in
42 p.b.w. of propylene glycol monomethyl ether-acetate.
Exposure: 36 mJ/cm$^2$ (KrF-excimer laser) Post-exposure bake: 90 seconds, 110° C., hotplate
Development: 60 seconds (0.02 N aqueous tetramethylammonium hydroxide solution)

Example 7

A light-sensitive recording material was prepared using a coating solution according to Example 1, with the modification that, in place of 2.5 p.b.w. of a cresol/formaldehyde resol (Bakelite® R5363), 2.0 p.b.w. of hexa-N-methoxymethyl-melamine were used.
Exposure: 18 mJ/cm$^2$ (KrF-excimer laser)
Development: 90 seconds

Example 8

A light-sensitive recording material was prepared using a coating solution according to Example 2, with the modification that, in place of 0.4 p.b.w. of 1,3,5-tris-methanesulfonyloxy-benzene, 0.6 p.b.w. of 2,4,6-tris[4-(2,2,2-trifluoroethyl)-benzenesulfonyloxy]benzophenone was used.
Exposure: 32 mJ/cm$^2$ (KrF-excimer laser)
Development: 90 seconds
Evaluation of the developed recording materials The resist structures obtained according to Examples 1 to 8 represented a defect-free, negative image of the mask with steep resist flanks, structures down to 0.50 µm and in some cases even smaller being reproduced in true detail.

A scanning electron-microscopic examination showed that the resist flanks were aligned perpendicular to the substrate surface.

The layer losses in the exposed resist areas were in all cases about 20 nm/minute or less.

Examples 9 and 10 (Comparison Examples)

The coating solution according to Example 7 was modified by replacing the multifunctional sulfonic acid ester used therein by an identical quantity of triphenylsulfonium hexafluorophosphate (Example 9) or 2-nitrobenzyl tosylate (Example 10). After exposure to radiation of 260 nm wavelength at an energy of 55 or 115 mJ/cm$^2$ respectively, structures were obtained which did not show any image differentiation useful in practice.

When the onium salt was used (Example 9), coating residues were also observed in the unexposed areas, i.e., resist residues adhered to the substrate in the unexposed areas, whereas, when the tosyl ester was used (Example 10), undercut resist profiles were visible which were removable, even with enhanced exposure, only at the expense of the reproduction accuracy. Acceptable structurings were thus not obtained in either case.

Example 11

For producing an offset printing plate, a mechanically roughened and pretreated aluminum foil was whirler-coated with a coating solution of the following composition:
7.5 p.b.w. of a cresol/formaldehyde novolak having a softening range from 105 to 120° C.,
2.5 p.b.w. of a cresol/formaldehyde resol (Bakelite® R5363),
1.0 p.b.w. of 2,4,6-tris-methanesulfonyloxy-benzophenone (prepared analogously to the Synthesis Example) and
0.05 p.b.w. of crystal violet base in
90 p.b.w. of propylene glycol monomethyl ether-acetate.

After drying, the layer (layer weight about 2.5 g/m²) was exposed for 45 seconds under a negative test original and, after storage for 10 minutes, the plate was heated for 2 minutes in a circulating-air oven at a temperature of 140° C. Development was carried out using a developer of the following composition:

0.5 p.b.w. of sodium hydroxide,
0.8 p.b.w. of sodium metasilicate×9 H₂O and
1.0 p.b.w. of 2-n-butoxyethanol in
97.7 p.b.w. of deionized water.

On development, a negative image of the original in true detail became visible. After rinsing with water, the plate was made ready for printing by wiping with 1% phosphoric acid. 150,000 perfect prints were obtained from this printing plate.

Example 12

For producing a dry etch- and negative electroplating-resist, a solution of the following composition was prepared:
12.5 p.b.w. of the novolak described in Example 11,
10.0 p.b.w. of hexa-N-methoxymethyl-melamine,
0.8 p.b.w. of 1,2,4-tris-ethanesulfonyloxybenzene (prepared analogously to the Synthesis Example) and
0.1 p.b.w. of crystal violet in
30 p.b.w. of butanone.

A 25 µm thick polyethylene terephthalate film usual for this purpose was coated with this solution to give a dry layer thickness of 18 µm. The surface of the dry resist film was laminated to a further polyethylene terephthalate film. After peeling off the cover film, the dry film was laminated under pressure and heat to a brass plate. After cooling and peeling off the support film, the plate was exposed through an original, good image contrast becoming visible. The material was stored for 10 minutes and then heated for 4 minutes at 95° C. The unexposed areas were spray-developed using a developer of the composition indicated in Example 11. The sheet was then etched through to the smooth flanks, using commercially available iron(III) chloride solution. The milled products obtained can be yet further processed before they are separated.

What is claimed is:

1. A negative-working radiation-sensitive mixture comprising:
    a) at least one compound which generates a strong acid under the action of actinic radiation, selected from a di-, tri- or tetrahydroxybenzene optionally substituted by one or more radicals R', or a polymer containing at least one of a di-, tri-, or tetrahydroxy phenyl radical; which is partially or fully esterified with sulfonic acids of the formula R—SO₃H, where R and R' may be the same or different, and R is a [($C_1$–$C_{10}$)alkyl], ($C_5$–$C_{10}$) cycloalkyl, ($C_6$–$C_{10}$)aryl, ($C_6$–$C_{10}$)aryl($C_1$–$C_{10}$)alkyl or ($C_3$–$C_9$)heteroaryl radical, any of which may be further substituted, and R' is one of the radicals given for R or is a ($C_1$–$C_{10}$)alkyl, ($C_1$–$C_{10}$)alkanoyl, ($C_1$–$C_{16}$)alkoxycarbonyl or ($C_7$–$C_{11}$)aroyl radical, any of which may be substituted,
    b) at least one compound having at least two groups crosslinkable by means of said strong acid, and
    c) at least one polymeric binder which is insoluble in water and soluble or at least swellable in an aqueous alkaline solution.

2. A negative-working radiation-sensitive mixture as claimed in claim 1, wherein (a) comprises a di- or tri-hydroxybenzene, optionally substituted with a radical R', which is fully esterified with, respectively, 2 or 3 sulfonic acids R—SO₃H.

3. A negative-working radiation-sensitive mixture as claimed in claim 1, wherein the radical R is substituted by at least one substituent selected from the group consisting of ($C_1$–$C_8$)alkyl, ($C_1$–$C_8$)alkoxy, ($C_1$–$C_8$)alkanoyl, ($C_1$–$C_8$) alkanoyloxy, ($C_6$–$C_{10}$)aryl, cyano, and halogen.

4. A negative-working radiation-sensitive mixture as claimed in claim 1, wherein the hydroxybenzene is substituted by R', and R' is an aromatic radical substituted by at least one substituent selected from the group consisting of ($C_1$–$C_8$)alkyl, ($C_1$–$C_8$)alkoxy, ($C_1$–$C_8$)alkanoyl, ($C_1$–$C_8$) alkanoyloxy, halogen and sulfonyloxy of the formula —O—SO₂—R'', wherein R'' is ($C_1$–$C_{10}$)alkyl, ($C_5$–$C_{10}$) cycloalkyl, ($C_6$–$C_{10}$)aryl, ($C_6$–$C_{10}$)aryl-($C_1$–$C_{10}$)alkyl or ($C_3$–$C_9$)heteroaryl radical, any of which may be further substituted.

5. A negative-working radiation-sensitive mixture as claimed in claim 1, comprising 0.5 to 25% by weight, of (a) based on the total weight of the solids in the mixture.

6. A negative-working radiation-sensitive mixture as claimed in claim 1, wherein (b) comprises a resol.

7. A negative-working radiation-sensitive mixture as claimed in claim 1, wherein (b) comprises an aromatic compound substituted by at least one of alkoxymethyl or oxiranylmethyl groups.

8. A negative-working radiation-sensitive mixture as claimed in claim 1, wherein (b) comprises a melamine/formaldehyde or urea/formaldehyde condensate.

9. A negative-working radiation-sensitive mixture as claimed in claim 1, comprising 1 to 50% by weight of (b) based on the total weight of solids in the mixture.

10. A negative-working radiation-sensitive mixture as claimed in claim 1, wherein (c) comprises at most 30% by weight of a novolak condensation resin.

11. A negative-working radiation-sensitive mixture as claimed in claim 1, wherein (c) comprises a polymer having at least one phenolic hydroxy groups.

12. A negative-working radiation-sensitive mixture as claimed in claim 1, wherein (c) has an extinction of <0.5 µm⁻¹, for radiation of 248 nm wavelength.

13. A negative-working radiation-sensitive mixture as claimed in claim 1, wherein the mixture comprises 40 to 95% by weight of (c), based on the total weight of solids in the mixture.

14. A negative-working radiation-sensitive mixture as claimed in claim 1, wherein said (a) comprises a polymer containing a di-, tri-, or tetra-hydroxyphenyl radical which has been partially or fully esterified with said sulfonic acid.

15. A negative-working radiation-sensitive mixture as claimed in claim 14, wherein said polymer before esterification is a condensation product of a tri-hydroxy benzene with a ketone.

16. A negative-working radiation-sensitive mixture as claimed in claim 1, wherein said (a) comprises said di-, tri-, or tetrahydroxybenzene which has been partially or fully esterfied with said sulfonic acid.

17. A negative-working radiation-sensitive recording material comprising a substrate bearing a radiation-sensitive layer which comprises a mixture as claimed in claim 1.

18. A process for producing the recording material as claimed in claim 17, comprising applying said mixture to said substrate so as to form a radiation-sensitive layer.

19. A process of preparing an image pattern which comprises irradiating the radiation-sensitive layer of the recording material of claim 17 imagewise, optionally heating the layer, treating the layer with a developer which dissolves and removes the non-irradiated areas of the layer, and optionally post-hardening the developed layer structures.

20. A process for producing a recording material as claimed in claim 17, which comprises coating said radiation-sensitive layer onto a temporary substrate, and applying said substrate to said radiation-sensitive layer, and then optionally removing said temporary substrate.

21. A negative-working radiation-sensitive mixture as claimed in claim 1, wherein R is a cycloalkyl or heteroaryl radical.

* * * * *